United States Patent
Ley et al.

(10) Patent No.: US 6,912,423 B2
(45) Date of Patent: Jun. 28, 2005

(54) TERMINAL CONNECTOR ASSEMBLY FOR A MEDICAL DEVICE AND METHOD THEREFOR

(75) Inventors: Gregory R. Ley, Blaine, MN (US); Gregory L. Sundberg, Stillwater, MN (US); Jaime L. Rugnetta, St. Anthony, MN (US); Mary S. Wentorf, Roseville, MN (US); Paul E. Zarembo, Vadnais Heights, MN (US); Christopher M. Zerby, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 42 days.

(21) Appl. No.: 10/226,374

(22) Filed: Aug. 21, 2002

(65) Prior Publication Data

US 2003/0074031 A1 Apr. 17, 2003

Related U.S. Application Data

(63) Continuation-in-part of application No. 09/738,401, filed on Dec. 15, 2000, now Pat. No. 6,643,550.
(60) Provisional application No. 60/313,893, filed on Aug. 21, 2001.

(51) Int. Cl.$^7$ ................................................ A61N 1/28
(52) U.S. Cl. .............................. 607/37; 607/38; 607/27; 607/119; 607/122; 607/126; 607/132; 607/116; 439/527; 439/585; 439/668; 439/736; 439/874; 439/877; 439/908
(58) Field of Search .............................. 607/37–38, 27, 607/116, 119, 122–123, 126, 132; 439/527, 585, 592, 668–669, 736, 874–875, 877, 908–909

(56) References Cited

U.S. PATENT DOCUMENTS

| | | | |
|---|---|---|---|
| 4,469,104 A | 9/1984 | Peers-Trevarton | 128/419 |
| 4,572,605 A | 2/1986 | Hess | 339/177 |
| 4,922,607 A | 5/1990 | Doan et al. | 29/879 |
| 4,934,367 A | 6/1990 | Daglow et al. | 439/527 |
| 4,971,057 A | 11/1990 | Theres | 128/419 |
| 5,012,807 A | 5/1991 | Stutz, Jr. | 128/419 |
| 5,070,605 A | 12/1991 | Daglow et al. | 29/842 |
| 5,076,270 A | 12/1991 | Stutz, Jr. | 128/419 |
| 5,231,996 A | 8/1993 | Bardy et al. | 128/785 |
| 5,267,564 A | 12/1993 | Barcel et al. | 128/634 |
| 5,304,219 A | 4/1994 | Chernoff et al. | 607/122 |
| 5,413,508 A * | 5/1995 | Obara | 439/729 |
| 5,843,141 A | 12/1998 | Bischoff et al. | 607/37 |
| 5,935,159 A * | 8/1999 | Cross et al. | 607/116 |
| 6,208,900 B1 | 3/2001 | Ecker et al. | 607/17 |
| 6,643,550 B2 | 11/2003 | Westlund et al. | |
| 2004/0093052 A1 | 5/2004 | Westlund et al. | |

OTHER PUBLICATIONS

"Frequently Asked Questions regarding Connector Task Force", *NASPE, Association for the Advancement of Medical Instrumentation. Pacemaker Committee, Connector Task Force, PAC/CTF–N248*, May 2002, 2 pgs.
"Proposed IS–4 Quadripolar Lead Connector Standard", *AAMI Connector Task Force Proposal for AAMI Work Item PC–73*, May 2002, 2 pgs.

* cited by examiner

*Primary Examiner*—Shawntina Fuqua
(74) *Attorney, Agent, or Firm*—Schwegman, Lundberg, Woessner & Kluth, P.A.

(57) ABSTRACT

A connector assembly of an electrophysiolgial device. The connector assembly includes a substrate forming a tube extending from a proximal end to a distal end an electrical circuit formed on the substrate, such as etching or printing, where the substrate is optionally non-conductive. In another option, the connector assembly includes clad wires and/or flexible circuits within an insulated terminal structure.

21 Claims, 13 Drawing Sheets

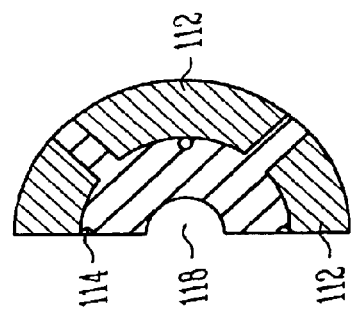
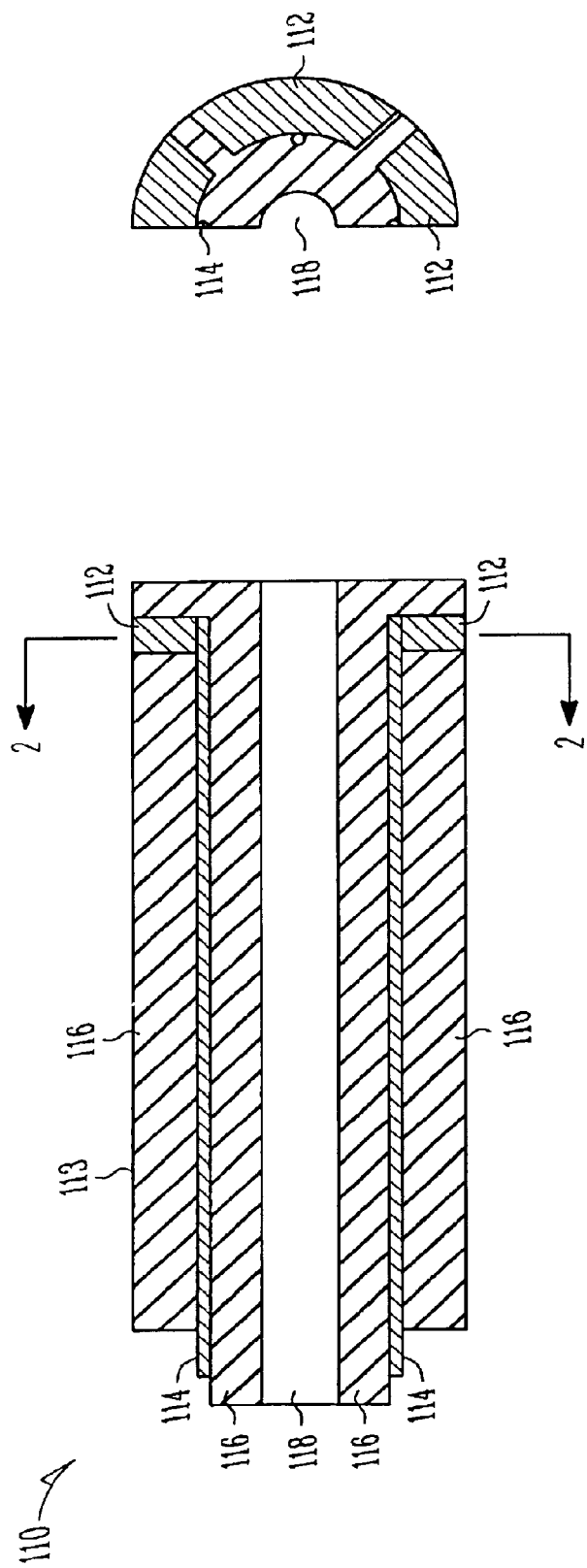
FIG. 1
FIG. 2

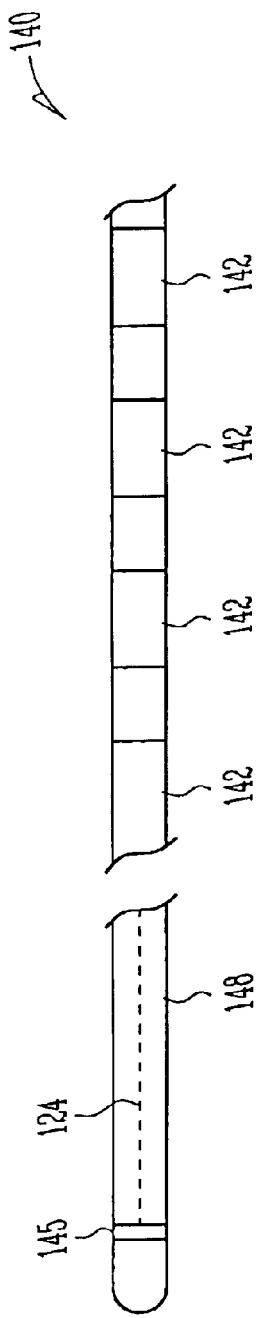
FIG. 11
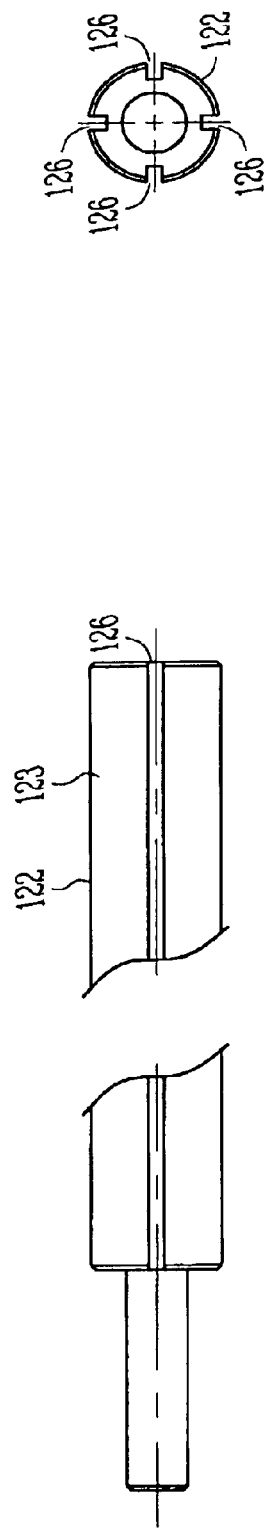
FIG. 13
FIG. 12

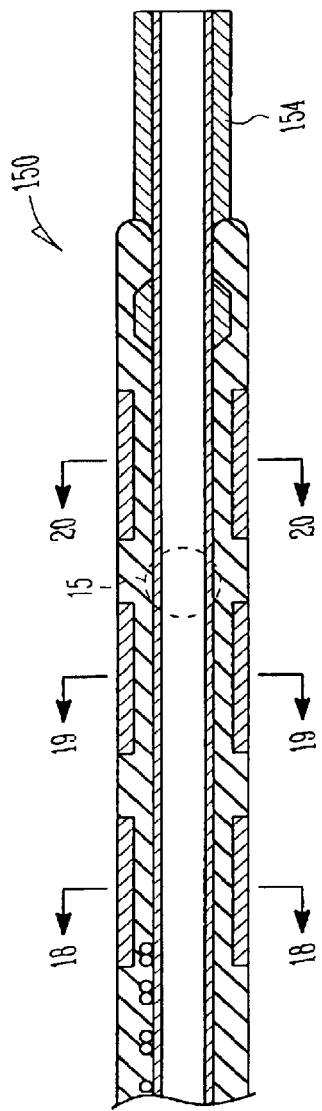
FIG. 17
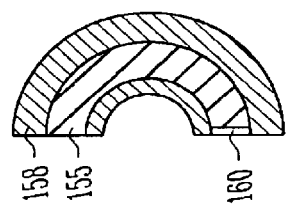
FIG. 20
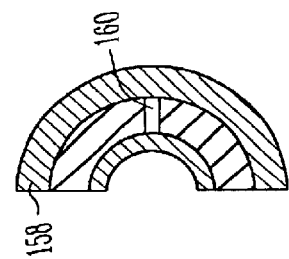
FIG. 19
FIG. 18

TERMINAL CONNECTOR ASSEMBLY FOR A MEDICAL DEVICE AND METHOD THEREFOR

CROSS-REFERENCE TO RELATED APPLICATION(S)

This application claims the benefit of U.S. Provisional Application No. 60/313,893, filed on Aug. 21, 2001, under 35 U.S.C. 119(e). This application is also a continuation-in-part of U.S. patent application Ser. No. 09/738,401, filed on Dec. 15, 2000 now U.S. Pat. No. 6,643,550, the specification of which are incorporated by reference herein.

TECHNICAL FIELD

The present invention relates generally to connector assemblies for electrophysiological applications. More particularly, it pertains to printed circuit and micro terminal connectors for electrophysiological applications.

BACKGROUND

Connector assemblies are used to couple electrophysiological devices with a conductor. For instance, a connector is used to couple a cardiac stimulator system such as a pacemaker, an anti-tachycardia device, a cardioverter or a defibrillator with a lead having an electrode for making contact with a portion of the heart.

When leads with multiple conductors are involved, the conductors are individually, mechanically and electrically coupled with the pulse generator at a proximal end of the multiple conductors. The multiple conductors at the proximal end are electrically insulated from each other to prevent shorts and limit electrical leakage between conductors. However, conventional assemblies are bulky and are relatively large for multi-polar assemblies. Furthermore, conventional assemblies have manufacturing drawbacks, for example, the assembly process is difficult and time consuming.

Accordingly, what is needed is an improved connector assembly. What is further needed is a multipolar connector having a reduced outer diamter.

SUMMARY

A connector assembly of an electrophysiologial device is provided herein which overcomes the above problems. The connector assembly includes an insulative elongate tube having an outer periphery and a longitudinal axis. The tube further includes at least one groove within the outer periphery of the elongate tube, and a conductor is disposed in each groove. The assembly further includes a conductive ring member with a projection extending from the internal surface. The projection of the ring member is disposed in the groove and is electrically coupled with the conductor. A terminal pin is disposed within the elongate tube, and insulative material is disposed over the insulative elongate tube adjacent to the conductive ring member.

In another embodiment, a micro terminal is provided that has an outer peripheral surface. The micro terminal includes a tube of insulation, and a first conductor embedded within the tube of insulation, a second conductor embedded within the tube of insulation. A first conductive tab and a second conductive tab extend from the outer peripheral surface to the first conductor and the second conductor, respectively. The tube of insulation has an inner lumen therethrough.

A method is also provided and includes forming a least one groove within an outer periphery of an insulative elongate tube having a longitudinal axis, disposing a conductor in each groove, placing at least one conductive ring member having an internal surface over the outer periphery of the insulative elongate tube, and disposing a projection extending from the internal surface of the conductive ring member within the at least one groove. The method further includes disposing a terminal pin within the insulative elongate tube, and disposing insulative material over the insulative elongate tube adjacent to the conductive ring member.

Several options are as follows. For instance, in one option, the method further includes disposing an insulated conductor in each groove, wherein a portion of insulation of the insulated conductor is removed as the insulated conductor is disposed within the groove. In another option, the method further includes forming a plurality of elongate grooves within the elongate tube, placing a plurality of conductive ring members over the outer periphery of the insulative elongate tube, and positioning the projection of each conductive ring member in a different groove from one another.

In another embodiment, a method includes mechanically and electrically coupling a plurality of conductors with a plurality of rings, positioning the rings and conductors around an inner tube, molding a insulation around the rings, the conductors, and inner tube, mechanically and electrically coupling a coil to a terminal pin, and disposing the coil and the terminal pin through the inner tube.

Several options for the method are as follows. For instance, in one option, the method further includes snap-fittedly coupling the terminal pin with the inner tube. In another option, the method further includes rotating the terminal pin with the inner tube after snap-fittedly coupling the terminal pin with the inner tube. In yet another option, the method further includes stringing an insulative lead body over the coil. Optionally, mechanically and electrically coupling the conductors with the rings includes staking the conductors with the rings.

The terminal connectors described herein allow for significantly smaller terminal design. Furthermore, an insulative non-conductive inner lumen has been provided, which is particularly suited for an open lumen lead, assisting in the prevention of electrical shorts due to fluid entry through the open lumen. In addition, the connectors lend themselves to isodiometric, over-the-wire lead designs, with multiple high and low voltage paths. Furthermore, the connector designs allow for the miniaturization of the connectors while simultaneously providing for multiple conductive pathways suitable for use in various lead designs. This further results in increased reliability and manufacturability of the designs with reduced resistance and increased isolative properties.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1 illustrates a side cut-away view of a connector assembly constructed in accordance with one embodiment.

FIG. 2 illustrates an end view of a connector assembly constructed in accordance with one embodiment.

FIG. 11 illustrates a side elevational view of a connector assembly constructed in accordance with one embodiment.

FIG. 12 illustrates a side-elevational view of a terminal pin in accordance with one embodiment.

FIG. 13 illustrates an end view of the terminal pin of FIG. 12.

FIG. 17 illustrates a cut-away view of a portion of a connector assembly constructed in accordance with one embodiment.

FIG. 18 illustrates a cross-section view of the connector assembly.

FIG. 19 illustrates a cross-section view of the connector assembly.

FIG. 20 illustrates a cross-section view of the connector assembly.

DESCRIPTION OF THE EMBODIMENTS

Figure 4:
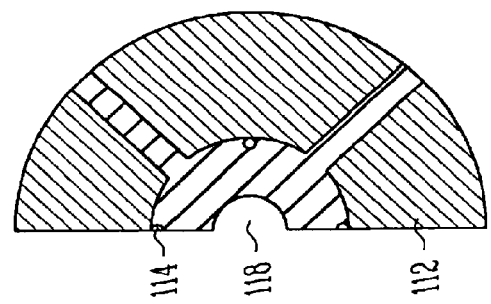
FIG. 4 illustrates an end view of a connector assembly in accordance with one embodiment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

A micro terminal connector assembly and a printed circuit connector assembly are provided herein. The micro terminal connector assembly includes small conductive insulated clad wires and/or flexible circuits which are fed through, or embedded within an insulated terminal structure. Variations on these designs include, but are not limited to, inclusion of elements of co-axial or co-radial lead technology. The printed circuit terminal assembly includes conductive and insulation layers in a multiple conductive terminal connector. Each of these in combinations thereof are described in further detail below.

FIGS. 1–4 illustrate examples of a feed-through terminal 110. The feed-through terminal 110 includes electrical connections which are fed from an outer surface of the terminal to the filars through an insulative material. The feed-through terminal 110 includes one or more metallic tabs 112 that serve to connect an outer surface 113 of the feed-through terminal 110 to conductor of the lead. The tabs 112, in one option, have different lengths. The tabs 112 advantageously provide a small feed-through connection between an outer peripheral surface and the conductor wire. The tabs 112 further allow for more insulation to be disposed between the tabs, as opposed to larger components, such as ring electrodes. This further allows the feed-through terminal 110 to have a smaller outer diameter and allows the feed-through terminal 110 to be used in high voltage applications.

A conductor wire 114 is electrically coupled with the tabs 112, for example, by welding to an inner side of the tabs 112. The wires 114 are formed of a conductive material, such as titanium, Pt—Ta, etc, and optionally the wires 114 are further individually insulated, in addition to the insulative material 116. The electrically connected wires 114 and tabs 112 are molded into an insulative material 116, such as tecothane, through a molding process, such as insert molding. Filars are welded, swaged, or connected using other connection processes to the wires 114 which, in one option, are fed through the terminal 110. The terminal 110 further includes an open lumen 118 therein, which has a wall formed of insulative material. A distal end of the wires 114, in one option, is exposed at a distal end of the insulation, as shown in FIG. 3, and conductive wires are attached thereto.

It should be noted that FIGS. 1 and 2 illustrate a co-radial design. In one option, a first conductor and a second conductor are embedded within the tube of insulation, and, optionally, are co-radial with one another. In another option, a first conductor, second, third, and fourth conductor are embedded within the tube of insulation, and are co-radial with one another.

Figure 3:
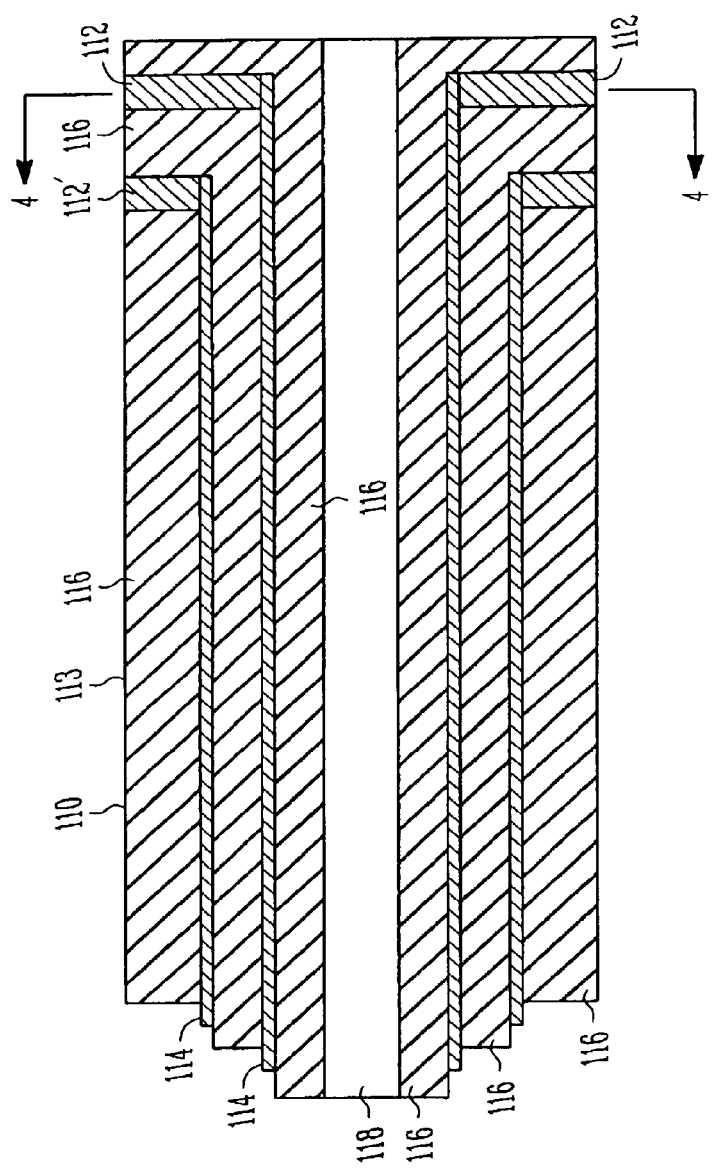
FIG. 3 illustrates a cut-away view of a connector assembly in accordance with another embodiment.

FIGS. 3 and 4 illustrate a coaxial design. For example, a first conductor is radially spaced apart from a second conductor, but they share an axis. In another option, the first conductor is disposed around the second conductor. The tabs 112, 112' of FIG. 3, are in one option, longitudinally spaced from one another. In FIGS. 3 and 4, three layers of insulation 116 are incorporated to form the insulated lumen 118, and to insulate the wires 114 from one another. It should be further noted that the embodiments shown in FIG. 1 through FIG. 4 can be combined with the embodiments discussed above and below.

Figure 5:
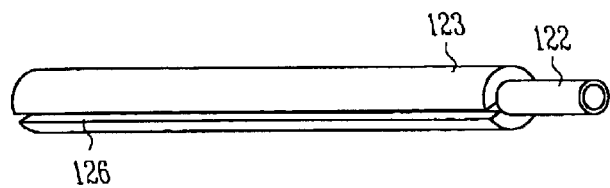
FIG. 5 illustrates a perspective view of a terminal pin in accordance with one embodiment.
Figure 6:
FIG. 6 illustrates a perspective view of a conductor in accordance with one embodiment.

FIGS. 5–8 illustrate one example of a bipolar feed-through terminal assembly 120 and portions thereof, incorporating another embodiment. The terminal assembly 120 includes a terminal pin 122. The terminal pin 122 is formed as a single unit of, in one option, insulative material, including an elongate tube 123. In another option, the terminal pin 122 and the elongate tube 123 are separate components coupled together, and optionally are formed of different materials. The elongate tube 123 is formed of insulative material, and includes at least one longitudinal groove 126 therein. In one option, the groove is an elongate longitudinal groove that is parallel to the longitudinal axis of the tube 123. Disposed within the longitudinal groove 126 is at least one conductor 124. One example of a conductor 124 is a flat elongate conductor, as shown in FIG. 6. Alternatively, other conductors such as wires, coils, or other shapes can be used as well. In another option, conductive material is coated within the groove 126 (FIG. 5). Optionally disposed over portions of the conductor 124 is additional insulative material, to insulate the conductor 124 from other rings or electrically conductive components which are slid thereover. In yet another option, the at least one conductor 124 extends continuously from the terminal pin to an electrode 145 along the lead body 148, as shown in FIG. 11.

Figure 9:
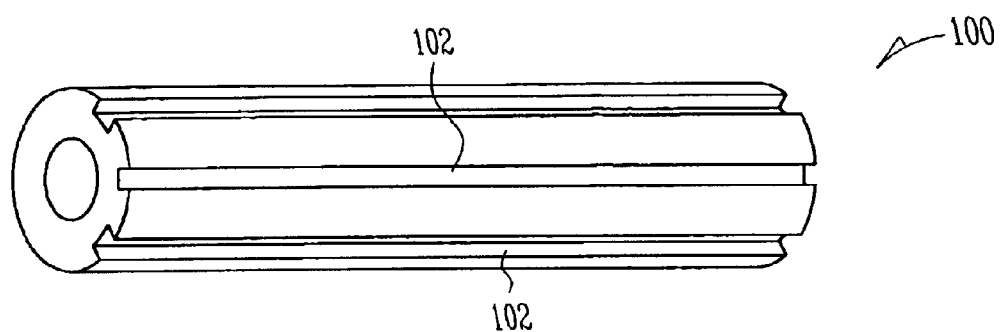
FIG. 9 illustrates a perspective view of a connector terminal constructed in accordance with one embodiment.
Figure 10:
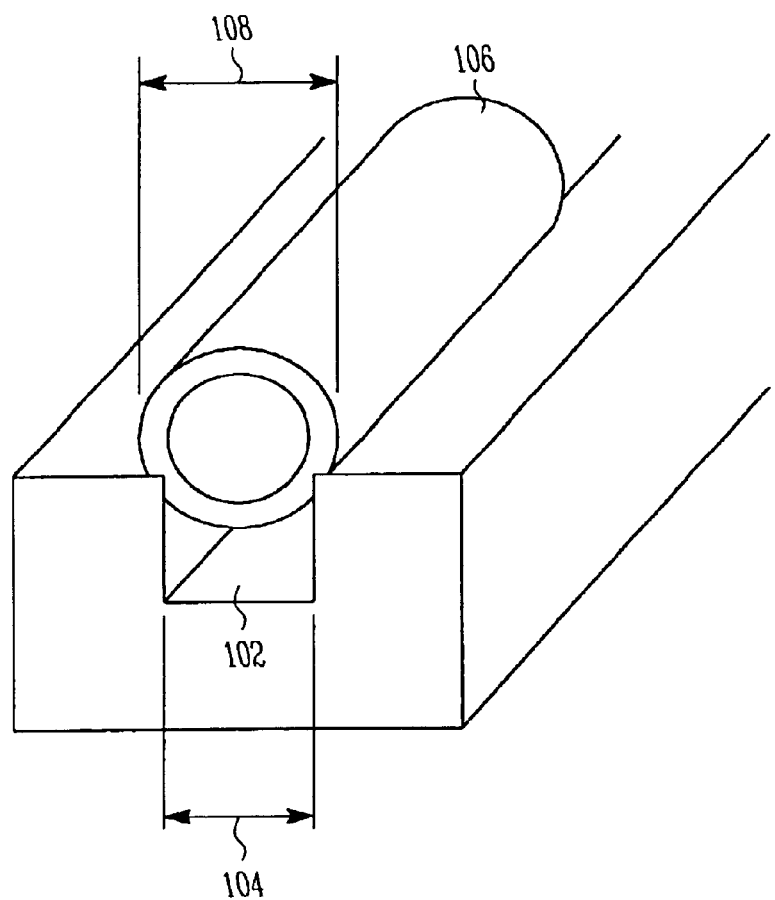
FIG. 10 illustrates a portion of a connector assembly in accordance with one embodiment.

FIGS. 9 and 10 illustrate another option for a terminal 100. The terminal 100 includes a plurality of grooves 102 formed therein. The grooves 102 are configured to receive an insulated filar 106 therein. The grooves have a width 104 which is slightly smaller than an outer diameter 108 of the filar 106. The filars 106 are forced into the groove 102. As the filars 106 are forced into the groove 102, the insulation of the filar 106 is removed, given the size of the width 104 for groove 102 relative to the filar 106. In one option, the terminal 100 is electrically conductive, and as the insulation of the filar 106 is removed, an electrical connection is made between the filar 106 and the terminal 100. In another option, the terminal 100 is formed of non-conductive material, such as polyetheretherketone (PEEK), and the filar 106 is electrically coupled with another component, such as a ring, as further described below.

In another option, the terminal 100 will consist of multiple strips of metal which are insert molded, into an insulating polymer. Alternatively, the multiple strips of metal are disposed within the insulative polymer in other manners. Each strip of metal will have the grooves 102 formed or cut therein which forms the insulation displacement connector. The strips are placed in locations to make connections with electrodes or rings, which are electrically coupled with a pulse generator. The insulation displacement terminal can be used with the various embodiments discussed above and below.

Figure 7:
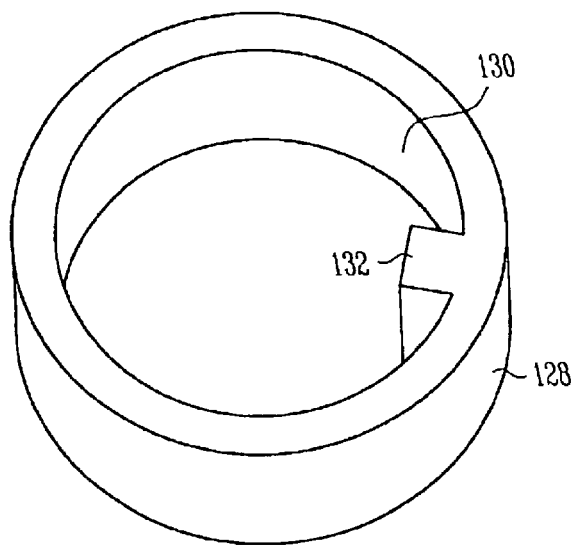
FIG. 7 illustrates a perspective view of a ring constructed in accordance with one embodiment.
Figure 8:
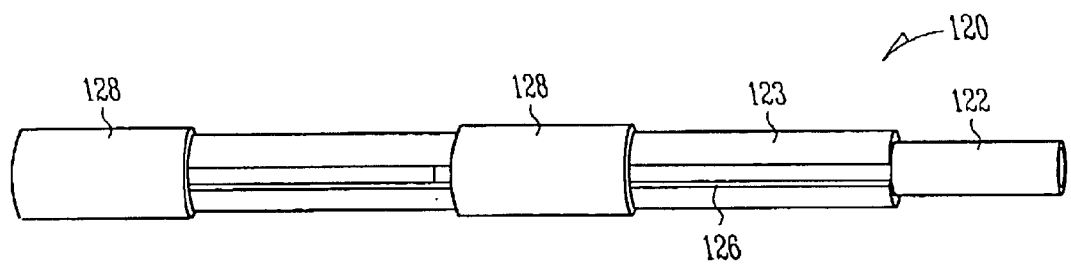
FIG. 8 illustrates a perspective view of a connector assembly in accordance with one embodiment.

Referring to FIGS. 7 and 8, the terminal assembly 120 further includes one or more electrically conductive rings 128. As shown in FIG. 7, the ring, in one option, has an interior surface 130 from which a projection 132 extends. The projection 132 of the ring 128 is received within the groove 126, and is electrically coupled with the conductor 124. The projection 132 electrically couples the conductor 124 with the header or other electrical stimulation device. FIG. 7 illustrates an example where multiple rings 128 are incorporated within the assembly 120.

Figure 14:
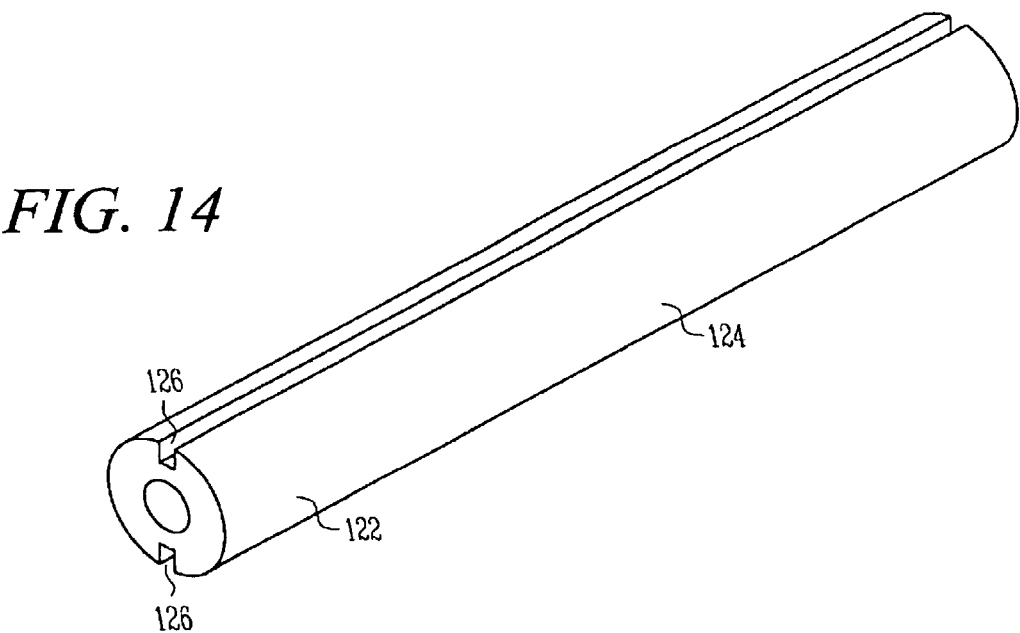
FIG. 14 illustrates a perspective view of a portion of a terminal pin constructed in accordance with one embodiment.
Figure 15:
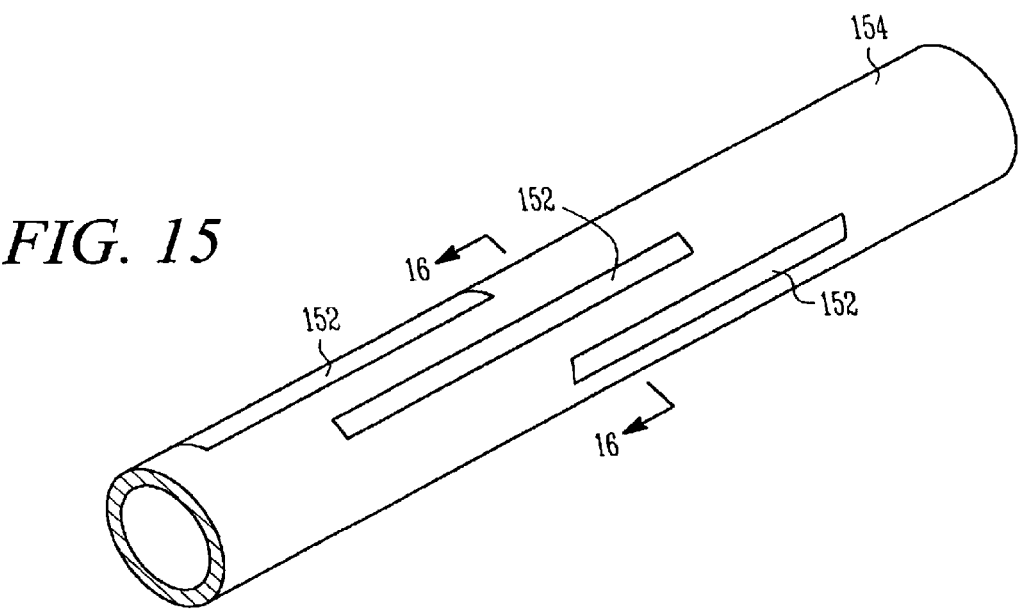
FIG. 15 illustrates a tube constructed in accordance with one embodiment.
Figure 16:
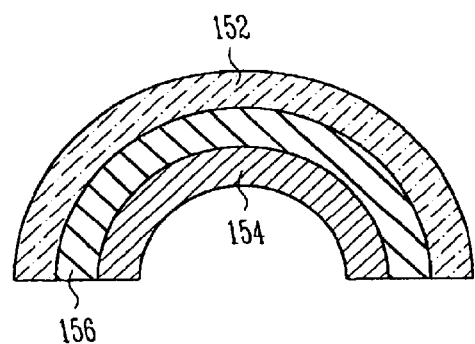
FIG. 16 illustrates a portion of cross-sectional view of the tube in FIG. 15.

FIGS. 11–13 illustrate alternative embodiments for the terminal pin 122. The elongate tube 123 of the terminal pin 122 includes a plurality of grooves 126 within the periphery of the elongate tube 123, for example, four grooves 126 suitable for use in a quad-polar design, shown in FIGS. 11–13. It should be noted that any number of grooves can be used, including a single groove. Alternatively, two grooves 126 are formed in the elongate tube of the terminal pin 122 (FIG. 14). At least one conductor 124 (FIG. 9) is inserted into each of the grooves 126. Since the grooves 126 are disposed within insulative material for the terminal pin 122, each of the conductors 124 are electrically isolated from one another, and do not add to the overall outer diameter of the terminal assembly 120.

FIG. 11 illustrates a connector assembly 140 formed from a terminal pin 122 of FIGS. 12 and 13. Four rings 142, each having an outer diameter of 0.072 inches, are disposed over the terminal pin 122, and each is electrically coupled with a conductor disposed within the grooves. An outer diameter of 0.072 inches is achievable due to the construction of the terminal pin 122 and ring 142. The inner diameter of the lumen is electrically isolated from each of the four rings 142, and the four rings 142 are electrically isolated from one another. All of the dielectric paths for this quad-polar configuration were confirmed to be electrically isolated at 1,500 volts AC. Previously, it was not possible to have a bipolar 0.072 inch outer diameter terminal.

FIGS. 15–20 illustrate another embodiment including a printed circuit terminal 150. The printed circuit terminal 150 includes one or more printed circuits 152 thereon. The printed circuits 152 or conductive paths would be printed on a substrate in the form of a tube 154, where the tube 154 is formed of non-conductive material. In another option, the tube 154 is formed of electrically conductive material. In another option, a layer of insulation 156 is disposed over the tube 154, and the printed circuits 152 are formed on the layer of insulation 156. In addition, a layer of insulation 155 is disposed in a layer over the printed circuits 152. One or more rings 158 are disposed on the assembly 150. An electrical connection 160 would then be formed in between the ring 158 and the printed circuits 152, where the electrical connection 160 is fed through the insulative material. Each of the individual printed circuits 152 would be electrically isolated from each other by the spacing on the insulative material 156. The printed circuits can be printed on the pin or substrate 154, alternatively they can be etched or otherwise formed thereon. One example of material for use with the insulative material is KAPTON™ by Dupont. Examples for the conductive material include, but are not limited to, gold, platinum, titanium, copper, or nickel. The connections in between the ring and the printed circuits are formed, for example, by an exposed pad with feed-through wires, a wire through hole, or fingers which extend beyond the flexible circuits, as further discussed above and below.

Figure 21:
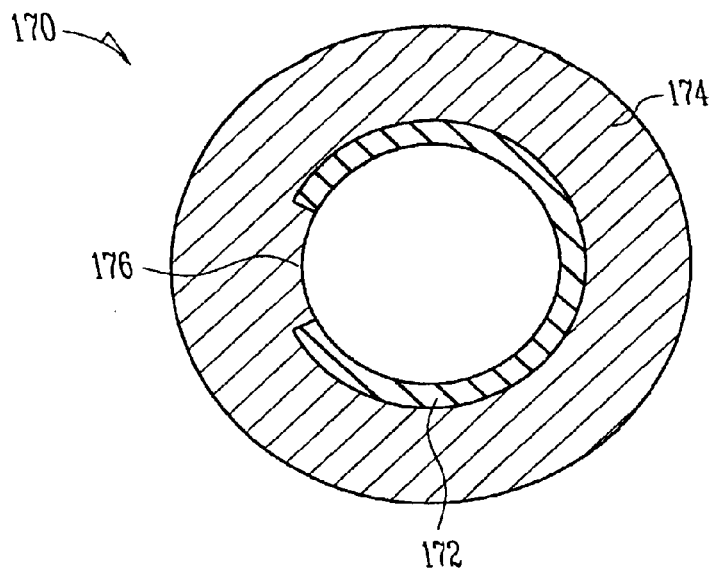
FIG. 21 illustrates a cross-sectional view of a portion of a connector assembly constructed in accordance with one embodiment.

FIG. 21 illustrates one example of connecting the etched pathways or conductive paths with the terminal by insulated rings 170 which are connected to set screws. The rings 170 have insulating material 172 such as polyurethane, silicone dioxide, etc., as the insulative material. The ring 170 further includes a conductive portion 174, which is formed of conductive material, such as, but not limited to, titanium, gold, or platinum. A small section 176 of an inside of a ring 170 is not insulated and can make an active connection with one of the etched conductive pathways (see 180, FIG. 22).

Figure 22:
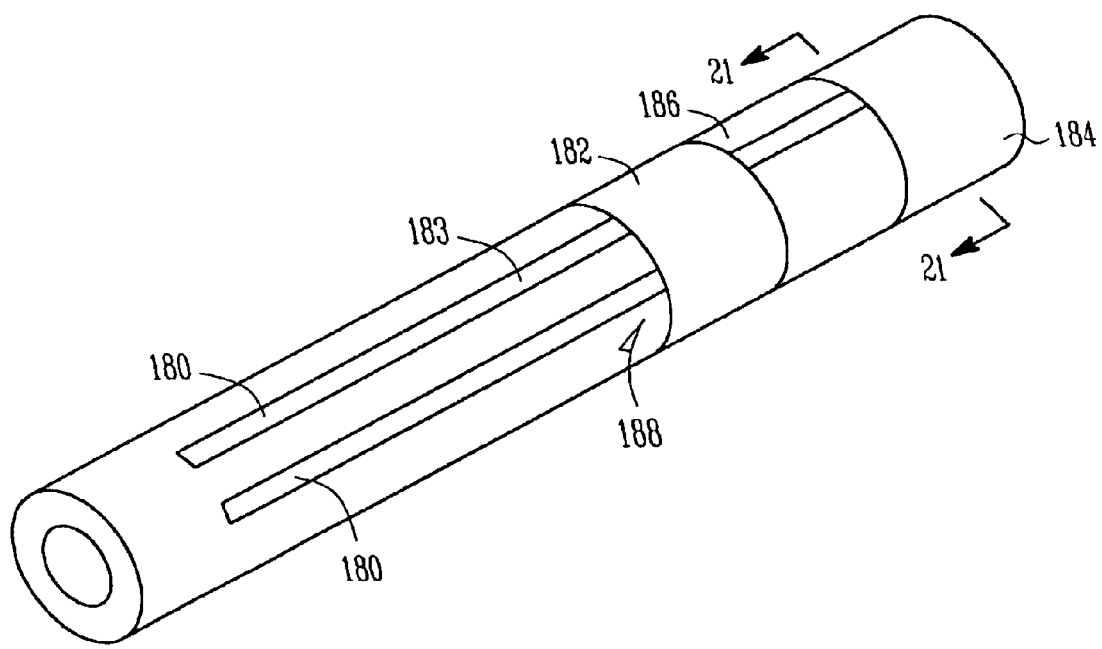
FIG. 22 illustrates a perspective view of a portion of a connector assembly constructed in accordance with one embodiment.
Figure 24:
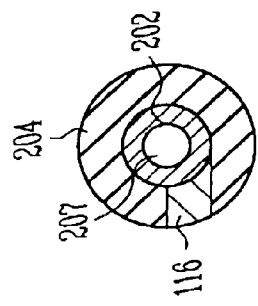
FIG. 24 illustrates a cut-away view of FIG. 23 constructed in accordance with one embodiment.

FIG. 22 illustrates another example of a printed circuit terminal which includes two etched pathways 180 thereon, including a first pathway 181 and a second pathway 183. The first pathway 181 and the second pathway 183 are electrically isolated from one another. It should be noted that additional pathways are contemplated and considered within the scope of this application. The first and second pathways 181, 183 are electrically coupled with a first ring 182 and a second ring 184, respectively. Ring 182 is electrically isolated at 186 such that it is isolated from the second pathway 183. Ring 182 is electrically coupled at 188 with the first pathway 181 to form the electrical connection thereto.

Figure 23:
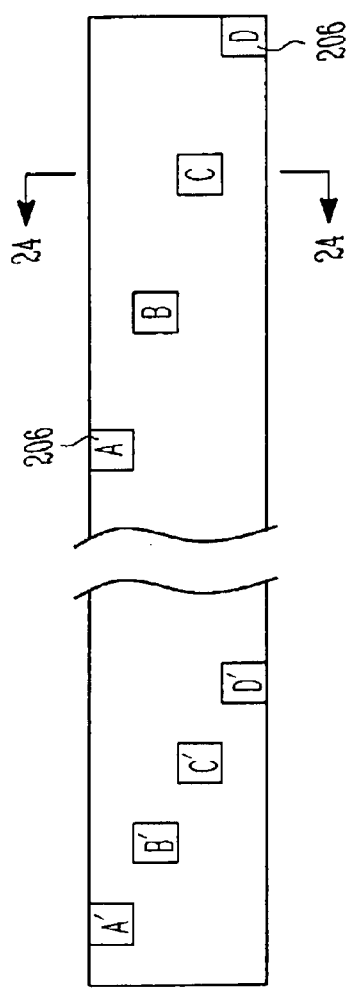
FIG. 23 illustrates a side view of a micro terminal constructed in accordance with one embodiment.
Figure 25:
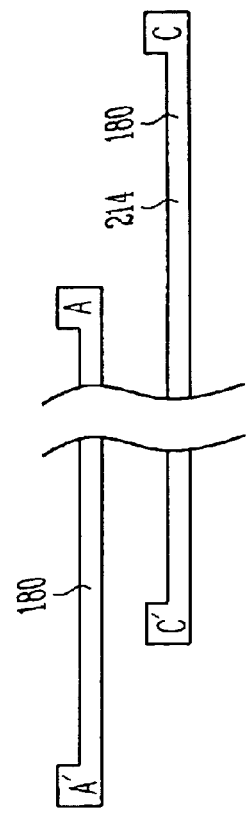
FIG. 25 illustrates a side view of the conductive pathways of FIG. 23 constructed in accordance with one embodiment.
Figure 26:
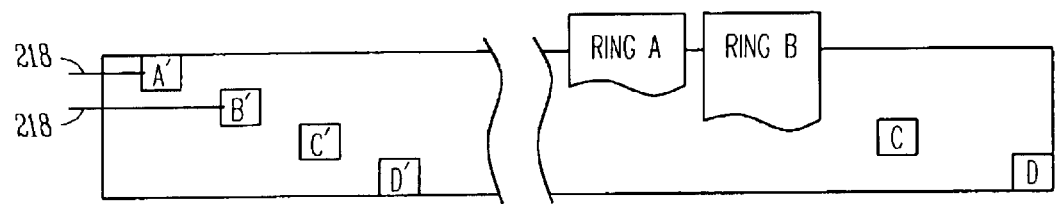
FIG. 26 illustrates a side view of a micro terminal assembly constructed in accordance with one embodiment.
Figure 27:
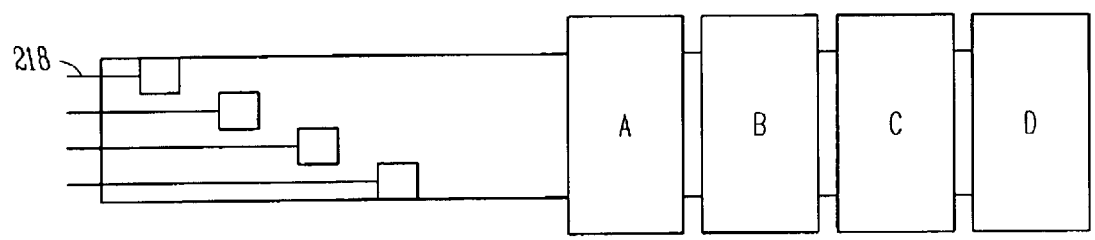
FIG. 27 illustrates a side view of a micro terminal assembly constructed in accordance with one embodiment.
Figure 28:
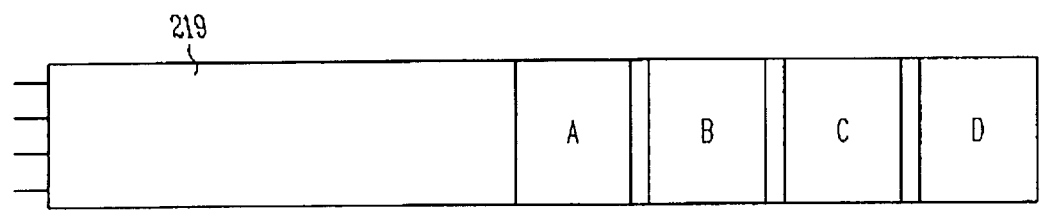
FIG. 28 illustrates a side view of a micro terminal assembly constructed in accordance with one embodiment.
Figure 29:
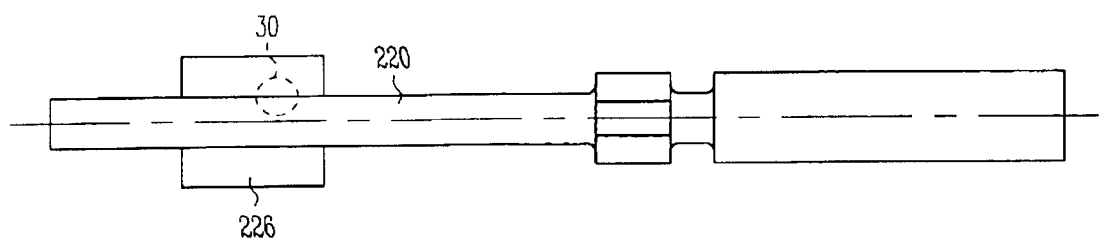
FIG. 29 illustrates a side-elevational view of a pin and ring assembly constructed in accordance with one embodiment.

FIG. 23 illustrates another variation of a micro terminal concept. A printed circuit terminal pin 200 includes a pin 202 and a layer of insulation 204 with a plurality of electrodes 206 therein. Optionally, pin 202 is formed of metal material The plurality of electrodes 206 are electrically isolated from one another within the layer of insulation 204. The plurality of electrodes 206 are coupled with conductive pathways 180 (FIG. 25) which are etched on the pin, and insulation 204 is disposed over the conductive pathways. The conductive pathways extend between the electrode 206 (A, B, C, and D) and the attachment sites, A', B', C', and D'. As shown in FIGS. 26 and 27, the rings, are coupled with their respective electrodes A, B, C, and D. Wires 218 are electrically coupled with the attachment sites A', B', C', and D' and extend along the lead body. As shown in FIG. 28, insulation 219 is disposed over insulation 204 and over attachment sites A', B', C', and D', and the terminal is optionally isodiametric. In another option, no rings are used, and the electrode 206 is used for electrical connection, for example, within a header. In another option, the wires 218 are embedded within the insulation 204, such that additional insulation 219 is not necessary. Still further, in another option, the conductive pathways comprise flexible circuits 214 which are disposed within the insulation. Electrical connection between the pin and the device is made by disposing electrical connectors 206 within the insulative material 216, where the electrical connectors 206 extend to various depths to reach the individual, respective flexible circuits 214. Filars of the lead are electrically coupled with a circuit trace of the flexible circuit 214. It should be noted that for this embodiment, as well as for above and below discussed embodiments, the flexible circuit 214 includes, but is not limited to, electrical paths which are printed, etched, or embedded within or on insulative material and formed into the appropriate configuration. In yet another option, the micro terminal includes a lumen 207.

Figure 30:
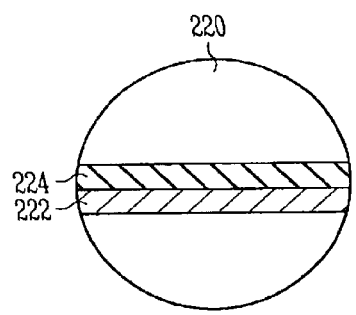
FIG. 30 illustrates a cross-sectional view of a portion of FIG. 29.
Figure 31:
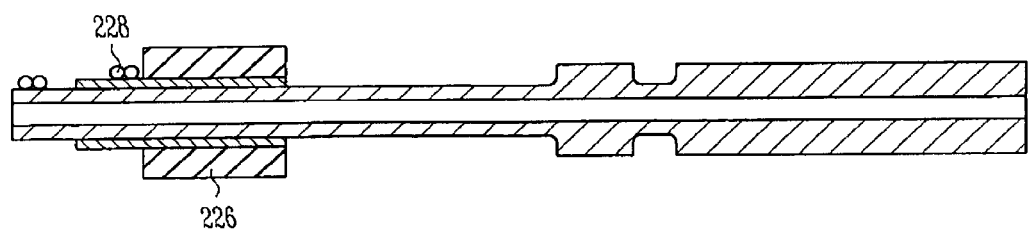
FIG. 31 illustrates a cross-sectional view of a connector assembly constructed in accordance with one embodiment.
Figure 35:
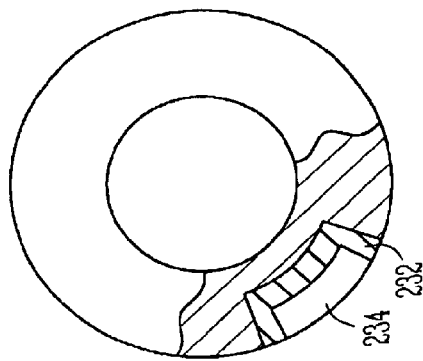
FIG. 35 illustrates a cross-sectional view of a connector assembly constructed in accordance with one embodiment.
Figure 34:
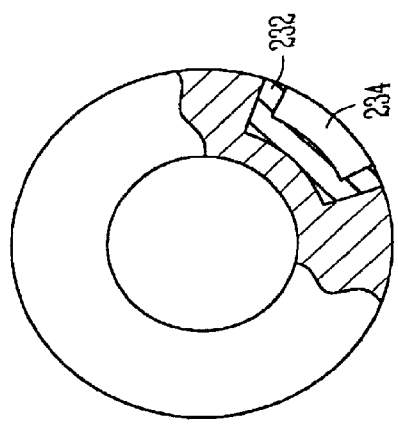
FIG. 34 illustrates a cross-sectional view of a connector assembly constructed in accordance with one embodiment.
Figure 33:
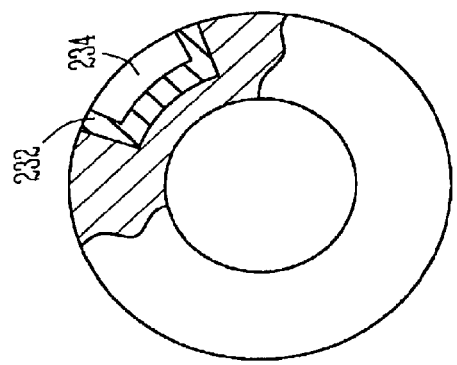
FIG. 33 illustrates a cross-sectional view of a connector assembly constructed in accordance with one embodiment.
Figure 32:
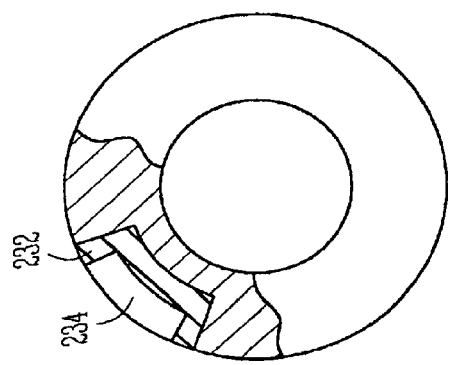
FIG. 32 illustrates a cross-sectional view of a connector assembly constructed in accordance with one embodiment.

FIGS. 30–31 illustrate another option of the printed circuit terminal. The printed circuit terminal includes, for example, a substrate 220, with a terminal ring disposed there over. A layer of insulative material, such as polyimid, i.e., KAPTON™ by Dupont, is disposed over the substrate 220. The layer of insulative material 222 has a thickness, for example, in the range of 0.0002 inches to 0.0010 inches. Disposed over the insulative material 222, is a layer for the conductive path 224. The layer 224, in one embodiment, comprises Pt, for the conductive path. The terminal ring 226 is slid over the layers of 224 and 222 and is joined with the outer conductive path 224 with, for example, by conductive adhesive, welding, or other fixation features which would form the electrical connection thereto. One or more filars 228 are electrically coupled with the outer conductive layer or path 224.

FIGS. 32–35 show one example of various cross-sectional views of the printed circuit tube for the terminal connector, for example, of a quad-polar. Each of the cross-section views include an insulative portion 232, as well as a conductor 234. Each of the conductors 234 shown individually in FIGS. 32–35 allow for the multiple rings to be electrically connected with the tube, for example, forming a quad polar relationship thereto, while also maintaining an isodiametric shape for the terminal pin. In addition, the FIGS. 32–35 illustrate how the conductors 234 are spaced peripherally from one another, for example, at 0, 90, 180, and 270 degrees around the diameter of the pin. In another option, the conductors 234 are longitudinally spaced from one another. It should be noted that other configurations, for example, with more or fewer electrically conductive portions can be configured and arranged on the printed circuit tube. It should be further noted that the embodiments shown in FIGS. 32–35 can be combined with all of the above discussed embodiments.

In another embodiment, a method for forming a connector assembly of an electrophysiological device is provided herein. The method includes insert molding a first flexible circuit within tubular insulating material, and electrically coupling a connector with the first flexible circuit. In one option, the method further includes molding a second flexible circuit within the tubular insulating material, where the second flexible circuit forms a second layer over the first flexible circuit. In another option, the method includes electrically coupling a second connector with the second flexible circuit, and the second connector has a different depth within the tubular insulating material than the first connector.

A method is also provided and includes forming a least one groove within an outer periphery of an insulative elongate tube having a longitudinal axis, disposing a conductor in each groove, placing at least one conductive ring member having an internal surface over the outer periphery of the insulative elongate tube, and disposing a projection extending from the internal surface of the conductive ring member within the at least one groove. The method further includes disposing a terminal pin within the insulative elongate tube, and disposing insulative material over the insulative elongate tube adjacent to the conductive ring member.

Several options are as follows. For instance, in one option, the method further includes disposing an insulated conductor in each groove, wherein a portion of insulation of the insulated conductor is removed as the insulated conductor is disposed within the groove. In another option, the method further includes forming a plurality of elongate grooves within the elongate tube, placing a plurality of conductive ring members over the outer periphery of the insulative elongate tube, and positioning the projection of each conductive ring member in a different groove from one another.

Figure 36:
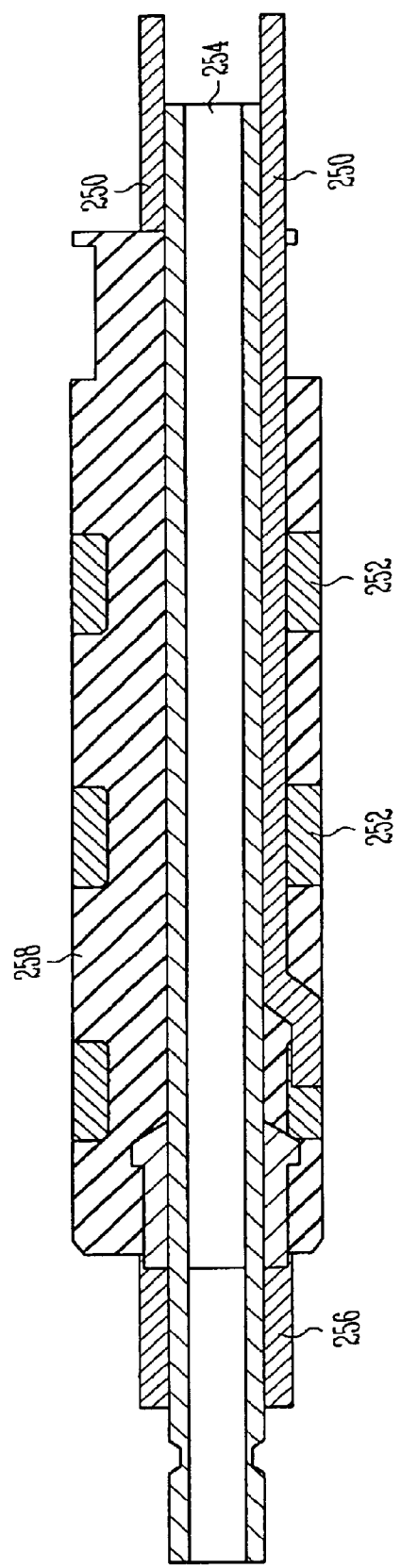
FIG. 36 illustrates a cross-section view of a connector assembly constructed in accordance with one embodiment.

In another embodiment, referring to FIG. 36, a method includes mechanically and electrically coupling a plurality of conductors 250 with a plurality of rings 252, for example, by staking the conductors 250 with the rings 252. The method further includes positioning the rings 252 and conductors 250 around an inner tube 254, molding an insulation 258 around the rings 252, the conductors 250, and inner tube 254, for example by injecting an insulative material to fix the components and place and complete the assembly except for the pin component. The rings, cables, and inner tube can be provided in a single overmolded assembly. The method further includes mechanically and electrically coupling a coil to a terminal pin 256, and disposing the coil and the terminal pin through the inner tube 254.

Several options for the method are as follows. For instance, in one option, the method further includes snap-fittedly coupling the terminal pin with the inner tube. In yet another option, the method further includes stringing an insulative lead body over the continuously extending conductors. Optionally, mechanically and electrically coupling the conductors with the rings includes coupling continuously extending conductors with the rings, and coupling the continuously extending conductors with an electrode (see FIG. 11). The method allows for achieving an outer diameter of approximately 3 mm, and in one option, is designed for a simple snap-assembly where latches of the pin and tube engage one another. Other types of snap-fit designs are available as well. The molding operation distinctly locates components consistently, and reliably isolates the conductors from one another by providing redundant insulation between components.

Advantageously, the above-described terminal connectors allow for significantly smaller terminal design. Furthermore, an insulative non-conductive inner lumen has been provided, which is particularly suited for an open lumen lead, assisting in the prevention of electrical shorts due to fluid entry through the open lumen. In addition, the above-described connectors lend themselves to isodiametric, over-the-wire lead designs, with multiple high and low voltage paths. Furthermore, the above connector designs allow for the miniaturization of the connectors while simultaneously providing for multiple conductive pathways suitable for use in various lead designs. This further results in increased reliability and manufacturability of the designs with reduced resistance and increased insulative properties.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A terminal assembly comprising:
   an insulative elongate tube having an outer periphery and a longitudinal axis;
   at least one groove within the outer periphery of the elongate tube;
   a conductor disposed in each groove;
   at least one conductive ring member having an internal surface;
   at least one projection extending from the internal surface of the conductive ring member, the projection disposed within the at least one groove and is electrically coupled with the conductor;
   a terminal pin extending from a pin proximal end to a pin distal end, the terminal pin disposed within the insulative elongate tube; and
   insulative material disposed over the insulative elongate tube adjacent to the conductive ring member.

2. The terminal assembly as recited in claim 1, further comprising a plurality of conductive ring members, each ring member having a projection extending from the internal surface, the insulative elongate tube having a plurality of grooves within the tube, each projection disposed in its respective groove.

3. The terminal assembly as recited in claim 1, further comprising a lead body mechanically coupled with the terminal pin, the lead body including an electrode thereon, wherein the at least one conductor extends continuously from the conductive ring member to the electrode.

4. The terminal assembly as recited in claim 1, wherein the at least one groove is an elongate groove extending generally parallel to the longitudinal axis of the insulative tube.

5. The terminal assembly as recited in claim 1, wherein the at least one conductor is an insulated conductor, and the insulated conductor is electrically coupled with the at least one conductive ring member.

6. The terminal assembly in claim 5, wherein an outer diameter of a portion of the insulated conductor is greater than a width of the at least one groove.

7. A micro terminal having an outer peripheral surface, the micro terminal comprising:
   a tube of insulation;
   a first conductor embedded within the tube of insulation;
   a second conductor embedded within the tube of insulation;
   a first conductive tab extending from the outer peripheral surface to the first conductor;
   a second conductive tab extending from the outer peripheral surface to the second conductor; and
   the tube of insulation having an inner lumen therethrough.

8. The micro terminal as recited in claim 7, wherein the first conductor and the second conductor are radially spaced apart from one another, and the first conductor is disposed around the second conductor.

9. The micro terminal as recited in claim 7, wherein the first conductor and the second conductor are co-radial with one another.

10. The micro terminal as recited in claim 7, further comprising a third conductor and a fourth conductor, and the first, second, third, and fourth conductors are co-radial with one another.

11. The micro terminal as recited in claim 7, wherein the first conductor and the second conductor are insulated conductors embedded within the tube of insulation.

12. The micro terminal as recited in claim 7, wherein the inner tube of insulation includes multiple layers of insulation.

13. The micro terminal as recited in claim 7, wherein the first tab has a first length, the second tab has a second length, and the first length is different than the second length.

14. The micro terminal as recited in claim 7, wherein the first conductor is a flexible circuit.

15. A method comprising:
    forming a terminal assembly including forming a least one groove within an outer periphery of an insulative elongate tube having a longitudinal axis;
    disposing a conductor in each groove;
    placing at least one conductive ring member having an internal surface over the outer periphery of the insulative elongate tube;
    disposing a projection extending from the internal surface of the conductive ring member within the at least one groove;

disposing a terminal pin within the insulative elongate tube; and disposing insulative material over the insulative elongate tube adjacent to the conductive ring member.

16. The method as recited in claim 15, further comprising disposing an insulated conductor in each groove, wherein a portion of insulation of the insulated conductor is removed as the insulated conductor is disposed within the groove.

17. The method as recited in claim 15, further comprising forming a plurality of elongate grooves within the elongate tube, placing a plurality of conductive ring members over the outer periphery of the insulative elongate tube, and positioning the projection of each conductive ring member in a different groove from one another.

18. A method comprising:

forming a terminal assembly including mechanically and electrically coupling a plurality of conductors with a plurality of rings;

positioning the rings and conductors around an inner tube;

molding insulation around the rings, the conductors, and inner tube;

mechanically and electrically coupling a coil to a terminal pin; and disposing the coil and the terminal pin through the inner tube.

19. The method as recited in claim 18, further comprising snap-fittedly coupling the terminal pin with the inner tube.

20. The method as recited in claim 18, wherein mechanically and electrically coupling the conductors with the rings includes coupling continuous conductors with the rings, and coupling the continuously extending conductors with an electrode.

21. The method as recited in claim 20, further comprising stringing an insulative lead body over the continuously extending conductors.

* * * * *

UNITED STATES PATENT AND TRADEMARK OFFICE
CERTIFICATE OF CORRECTION

PATENT NO. : 6,912,423 B2
APPLICATION NO. : 10/226374
DATED : June 28, 2005
INVENTOR(S) : Ley et al.

Page 1 of 1

It is certified that error appears in the above-identified patent and that said Letters Patent is hereby corrected as shown below:

On Title Page, Item (75) Col. 1, under "Inventors", in column 1, line 3, delete "St. Anthony" and insert -- White Bear Lake --, therefor.

Signed and Sealed this

Eighth Day of August, 2006

JON W. DUDAS
*Director of the United States Patent and Trademark Office*